United States Patent
Limbach et al.

(10) Patent No.: US 10,822,297 B2
(45) Date of Patent: Nov. 3, 2020

(54) METHOD FOR PRODUCTION OF METHYL METHACRYLATE BY OXIDATIVE ESTERIFICATION USING A HETEROGENEOUS CATALYST

(71) Applicants: Rohm and Haas Company, Collegeville, PA (US); Dow Global Technologies LLC, Midland, MI (US)

(72) Inventors: Kirk W. Limbach, Dresher, PA (US); Justin Walker, Midland, MI (US); Alan L. Stottlemyer, Midland, MI (US); Jeffrey Herron, Midland, MI (US)

(73) Assignees: Dow Global Technologies LLC, Midland, MI (US); Rohm and Haas Company, Collegeville, PA (US)

( * ) Notice: Subject to any disclaimer, the term of this patent is extended or adjusted under 35 U.S.C. 154(b) by 0 days.

(21) Appl. No.: 16/632,562

(22) PCT Filed: Jun. 25, 2018

(86) PCT No.: PCT/US2018/039239
§ 371 (c)(1),
(2) Date: Jan. 21, 2020

(87) PCT Pub. No.: WO2019/022890
PCT Pub. Date: Jan. 31, 2019

(65) Prior Publication Data
US 2020/0157035 A1    May 21, 2020

Related U.S. Application Data

(60) Provisional application No. 62/538,240, filed on Jul. 28, 2017.

(51) Int. Cl.
*C07C 67/40* (2006.01)
*C07C 69/54* (2006.01)

(52) U.S. Cl.
CPC .............. *C07C 67/40* (2013.01); *C07C 69/54* (2013.01)

(58) Field of Classification Search
CPC ......... C07C 67/39; C07C 45/75; C07C 69/54; B01J 23/89; B01J 23/44
See application file for complete search history.

(56) References Cited

U.S. PATENT DOCUMENTS

| | | | |
|---|---|---|---|
| 4,249,019 A | 2/1981 | Tamura et al. | |
| 4,518,796 A | 5/1985 | Aoshima et al. | |
| 4,520,125 A | 5/1985 | Baer et al. | |
| 5,969,178 A | 10/1999 | Okamoto et al. | |
| 6,040,472 A | 3/2000 | Yamamatsu et al. | |
| 6,228,800 B1 | 5/2001 | Yamaguchi et al. | |
| 7,326,806 B2 | 2/2008 | Hayashi et al. | |
| 8,461,373 B2 | 6/2013 | Suzuki et al. | |
| 8,614,349 B2 | 12/2013 | Yokota et al. | |
| 9,511,351 B2 | 12/2016 | Feaviour | |
| 9,617,199 B2 | 4/2017 | Krill et al. | |
| 2011/0184206 A1* | 7/2011 | Suzuki | B01J 23/755 560/103 |
| 2016/0251301 A1 | 9/2016 | Krill et al. | |
| 2016/0280628 A1 | 9/2016 | Krill et al. | |
| 2019/0099731 A1* | 4/2019 | Lygin | B01J 8/226 |

FOREIGN PATENT DOCUMENTS

| | | |
|---|---|---|
| CN | 1931824 A | 3/2007 |
| JP | S58185540 A | 10/1983 |
| JP | 2003048863 A | 2/2003 |
| WO | 2017084969 | 5/2017 |

* cited by examiner

Primary Examiner — Jafar F Parsa
(74) Attorney, Agent, or Firm — Brian L. Mutschler

(57) ABSTRACT

A method for preparing methyl methacrylate from methacrolein and methanol; said method comprising contacting in a reactor a mixture comprising methacrolein, methanol and oxygen with a catalyst bed of heterogeneous catalyst comprising a support and a noble metal, wherein base is added to the reactor while maintaining time to reach 95% homogeneity at no greater than 10 minutes.

10 Claims, No Drawings

METHOD FOR PRODUCTION OF METHYL METHACRYLATE BY OXIDATIVE ESTERIFICATION USING A HETEROGENEOUS CATALYST

BACKGROUND OF THE INVENTION

The invention relates to a method for preparing methyl methacrylate from methacrolein and methanol using a heterogeneous catalyst.

Methyl methacrylate has been produced by oxidative esterification reactions in which decreases in pH of the reaction mixture are known to be detrimental. The prior art reports that addition of base to the reactor to raise pH increases catalyst life and may reduce selectivity. The solution to this problem has been to mix the base into a portion of the reaction mixture or reactants in a separate vessel, see, e.g., U.S. Pub. No. 2016/0251301. However, there is a need for a more efficient process which can provide improved selectivity.

SUMMARY OF THE INVENTION

The present invention is directed to a method for preparing methyl methacrylate from methacrolein and methanol; said method comprising contacting in a reactor a mixture comprising methacrolein, methanol and oxygen with a catalyst bed of heterogeneous catalyst comprising a support and a noble metal, wherein base is added to the reactor while maintaining time to reach 95% homogeneity at no greater than 10 minutes.

DETAILED DESCRIPTION OF THE INVENTION

All percentage compositions are weight percentages (wt %), and all temperatures are in ° C., unless otherwise indicated. A noble metal is any of gold, platinum, iridium, osmium, silver, palladium, rhodium and ruthenium. More than one noble metal may be present in the catalyst, in which case the limits apply to the total of all noble metals. The "catalyst center" is the centroid of the catalyst particle, i.e., the mean position of all points in all coordinate directions. A diameter is any linear dimension passing through the catalyst center and the average diameter is the arithmetic mean of all possible diameters. The aspect ratio is the ratio of the longest to the shortest diameters.

Preferred bases include alkali metal hydroxides and $C_1$-$C_4$ alkoxides, preferably sodium and potassium hydroxide and sodium or potassium methoxide or ethoxide, preferably sodium hydroxide or sodium methoxide. Preferably, base is added as a solution, preferably in methanol, ethanol or water; preferably methanol or water. Preferably, alkoxides are added in methanol or ethanol.

Time to reach 95% homogeneity is calculated by the following equation for stirred reactors in turbulent flow:

$$\theta_{95} = 5.20 \frac{T^{1.5} H^{0.5}}{D^2 N_p^{1/3} N}$$

wherein T is inner reactor diameter, H is liquid height, D is impeller diameter, $N_p$ is characteristic power number of the impeller and N is the impeller speed in RPM.

Mixing time may be measured via several techniques. For transparent liquids and vessels, mixing time may be estimated using dye injections or decolorization techniques, with the 95% mixing time calculated using automated image processing algorithms. For opaque liquids or containers, other techniques utilizing conductivity, thermal, or pH probes may be utilized in combination with injections of conductive solutions, heat, or acids/bases respectively. A detailed discussion of techniques is provided by Brown et al, 2004, D. A. R. Brown, P. N. Jones, J. C. Middleton; Experimental methods, Part A: measuring tools and techniques for mixing and flow visualization studies; E. L. Paul, V. A. Atiemo-Obeng, S. M. Kresta (Eds.), Handbook of Industrial Mixing, Wiley-Interscience, Hoboken, NJ (2004), pp. 145-202.

Preferably, $\theta_{95}$ is no greater than 6 minutes, preferably no greater than 4 minutes, preferably no greater than 2 minutes, preferably no greater than 1 minute. Preferably, the reactor is a continuous stirred tank reactor. In a preferred embodiment, the reactor is jet mixed vessel.

Preferably, superficial velocity of liquid through the catalyst bed is from 0.1 to 100 mm/s; preferably at least 1 mm/s, preferably at least 2 mm/s, preferably at least 3 mm/s, preferably at least 5 mm/s; preferably no greater than 20 mm/s, preferably no greater than 15 mm/s, preferably no greater than 12 mm/s, preferably no greater than 10 mm/s.

Preferably, the reactor has at least one impeller, preferably at least two impellers on one shaft. Preferably, the linear tip speed of the impeller is from 0.1 to 10 m/s; preferably at least 0.2 m/s, preferably at least 0.5 m/s, preferably at least 1 m/s, preferably at least 2 m/s; preferably no greater than 8 m/s, preferably no greater than 6 m/s. Preferably, the specific energy dissipation, c is from 0 to 2 W/kg; preferably at least 0.5 W/kg, preferably at least 1.0 W/kg; preferably no more than 1.8 W/kg, preferably no more than 1.6 W/kg. Preferably, H/T for the reactor is at least 1.2, preferably at least 1.3, preferably at least 1.4; preferably no greater than 2.2, preferably no greater than 2.0, preferably no greater than 1.8.

Preferably, oxygen concentration at a reactor outlet is from 0.5 to 7.5 mol %; preferably at least 1 mol %; preferably no greater than 6 mol %, preferably no greater than 5 mol %.

Preferably, the support is a particle of an oxide material; preferably γ-, δ-, or θ- alumina, silica, magnesia, titania, zirconia, hafnia, vanadia, niobium oxide, tantalum oxide, ceria, yttria, lanthanum oxide or a combination thereof. Preferably, in portions of the catalyst comprising the noble metal, the support has a surface area greater than 10 m$^2$/g, preferably greater than 30 m$^2$/g, preferably greater than 50 m$^2$/g, preferably greater than 100 m$^2$/g, preferably greater than 120 m$^2$/g. In portions of the catalyst which comprise little or no noble metal, the support may have a surface area less than 50 m$^2$/g, preferably less than 20 m$^2$/g.

Preferably, the aspect ratio of the catalyst particle is no more than 10:1, preferably no more than 5:1, preferably no more than 3:1, preferably no more than 2:1, preferably no more than 1.5:1, preferably no more than 1.1:1. Preferred shapes for the catalyst particle include spheres, cylinders, rectangular solids, rings, multi-lobed shapes (e.g., cloverleaf cross section), shapes having multiple holes and "wagon wheels;" preferably spheres. Irregular shapes may also be used.

Preferably, at least 90 wt % of the noble metal(s) is in the outer 70% of catalyst volume (i.e., the volume of an average catalyst particle), preferably the outer 60% of catalyst volume, preferably the outer 50%, preferably the outer 40%, preferably the outer 35%, preferably in the outer 30%, preferably in the outer 25%. Preferably, the outer volume of any particle shape is calculated for a volume having a constant distance from its inner surface to its outer surface (the surface of the particle), measured along a line perpendicular to the outer surface. For example, for a spherical particle the outer x % of volume is a spherical shell whose outer surface is the surface of the particle and whose volume is x % of the volume of the entire sphere. Preferably, at least 95 wt % of the noble metal is in the outer volume of the catalyst, preferably at least 97 wt %, preferably at least 99 wt %. Preferably, at least 90 wt % (preferably at least 95 wt %, preferably at least 97 wt %, preferably at least 99 wt %) of the noble metal(s) is within a distance from the surface that is no more than 30% of the catalyst diameter, preferably no more than 25%, preferably no more than 20%, preferably no more than 15%, preferably no more than 10%, preferably no more than 8%. Distance from the surface is measured along a line which is perpendicular to the surface.

Preferably, the noble metal is gold or palladium, preferably gold.

Preferably, the average diameter of the catalyst particle is at least 200 microns, preferably at least 300 microns, preferably at least 400 microns, preferably at least 500 microns, preferably at least 600 microns, preferably at least 700 microns, preferably at least 800 microns; preferably no more than 30 mm, preferably no more than 20 mm, preferably no more than 10 mm, preferably no more than 5 mm, preferably no more than 4 mm The average diameter of the support and the average diameter of the final catalyst particle are not significantly different.

Preferably, the catalyst is produced by precipitating the noble metal from an aqueous solution of noble metal salt in the presence of the support. In one embodiment of the invention, the catalyst is produced by incipient wetness in which an aqueous solution of a suitable noble metal precursor salt is added to a porous inorganic oxide such that the pores are filled with the solution and the water is then removed by drying. Preferred noble metal salts include tetrachloroauric acid, gold thiosulfate, aurothiomalate, gold hydroxide, palladium nitrate, palladium chloride and palladium acetate. The resulting material is then converted into a finished catalyst by calcination, reduction, or other treatments known to those skilled in the art to decompose the noble metal salts into metals or metal oxides. Preferably, a $C_2$-$C_{18}$ thiol comprising at least one hydroxyl or carboxylic acid substituent is present in the solution. Preferably, the $C_2$-$C_{18}$ thiol comprising at least one hydroxyl or carboxylic acid substituent has from 2 to 12 carbon atoms, preferably 2 to 8, preferably 3 to 6. Preferably, the thiol compound comprises no more than 4 total hydroxyl and carboxylic acid groups, preferably no more than 3, preferably no more than 2. Preferably, the thiol compound has no more than 2 thiol groups, preferably no more than one. If the thiol compound comprises carboxylic acid substituents, they may be present in the acid form, conjugate base form or a mixture thereof. The thiol component also may be present either in its thiol (acid) form or its conjugate base (thiolate) form. Especially preferred thiol compounds include thiomalic acid, 3-mercaptopropionic acid, thioglycolic acid, 2-mercaptoethanol and 1-thioglycerol, including their conjugate bases.

In one embodiment of the invention, the catalyst is produced by deposition precipitation in which a porous inorganic oxide is immersed in an aqueous solution containing a suitable noble metal precursor salt and that salt is then made to interact with the surface of the inorganic oxide by adjusting the pH of the solution. The resulting treated solid is then recovered (e.g. by filtration) and then converted into a finished catalyst by calcination, reduction, or other pre-treatments known to those skilled in the art to decompose the noble metal salts into metals or metal oxides.

This invention is useful in a process for producing methyl methacrylate (MMA) which comprises treating methacrolein with methanol in an oxidative esterification reactor (OER) containing a catalyst bed. The catalyst bed comprises the catalyst particles and is situated within the OER such that liquid flow may occur between the catalyst bed and the reactor walls. The OER further comprises a liquid phase comprising methacrolein, methanol and MMA and a gaseous phase comprising oxygen. The liquid phase may further comprise byproducts, e.g., methacrolein dimethyl acetal (MDA) and methyl isobutyrate (MIB). Preferably, the liquid phase is at a temperature from 40 to 120° C.; preferably at least 50° C., preferably at least 60° C.; preferably no more than 110° C., preferably no more than 100° C. Preferably, the catalyst bed is at a pressure from 0 to 2000 psig (101 to 14 MPa); preferably no more than 2000 kPa, preferably no more than 1500 kPa. Preferably, pH in the catalyst bed is from 4 to 10; preferably at least 5, preferably at least 5.5; preferably no greater than 9, preferably no greater than 8, preferably no greater than 7.5. Preferably, the catalyst bed is in a tubular continuous reactor or a continuous stirred tank reactor. Preferably, the catalyst bed further comprises oxygen gas.

The catalyst particles in the catalyst bed typically are held in place by solid walls and by screens or catalyst support grids. In some configurations, the screens or grids are on opposite ends of the catalyst bed and the solid walls are on the side(s), although in some configurations the catalyst bed may be enclosed entirely by screens. Preferred shapes for the catalyst bed include a cylinder, a rectangular solid and a cylindrical shell; preferably a cylinder. Preferably, the reactor comprises a catalyst bed situated to allow liquid flow through the catalyst bed. Preferably, the catalyst bed is in a tubular continuous reactor or a continuous stirred tank reactor (CSTR); preferably a tubular continuous reactor; preferably the bed is cylindrical. When the catalyst bed is in a CSTR, preferably, the reactor comprises a stack, which is a vertical solid partition having an inside and an outside (i.e., its cross-section perpendicular to the height is a continuous closed curve), allowing liquid flow upward on one side of the stack (e.g., inside or outside) and downward on the other side. In a preferred embodiment the catalyst bed is in the shape of a substantially cylindrical shell located between the stack and the reactor walls. The stack may be a cylindrical shell (cylinder with a cylindrical hole), a rectangular shell or a more complex shape, e.g., a shape derived from a cylindrical shell by flaring the sides outward (toward the reactor walls) at the ends or a shape having an outer or inner surface of a cylindrical shell but with tapering on the other surface to produce a variable thickness; preferably a cross section of the stack perpendicular to the height consists of two or more concentric circles. Preferably, the stack is centered in the reactor. Preferably, the stack is stationary relative to the reactor walls. Preferably, the long dimension of the stack is from 30 to 80% of the long dimension of the reactor, preferably from 40 to 75%. Preferably, the maximum cross-section diameter of the stack is from 40 to 90% of the diameter of the reactor, preferably at least 45%, preferably at least 50%, preferably no more than 85%, preferably no more than 80%. In a preferred embodiment in which the reactor is a continuous stirred tank reactor (CSTR), the height of the stack is from 30 to 80% of the height of the reactor; preferably at least 40%, preferably no more than 75%, preferably no more than 70%. In a CSTR, preferably the height of the catalyst bed is from 30 to 90% of the height of the stack, preferably at least 40%, preferably no more than 80%. Preferably, the sides of the catalyst bed are in contact with the stack.

Preferably, the CSTR is configured with the catalyst bed between the stack and the reactor walls with liquid flow downward inside the stack and upward through the catalyst bed. Preferably gaseous reactants and inert (oxygen, nitrogen, carbon dioxide) rise upward through the catalyst bed.

Preferably, the contents of the reactor are mixed, either by at least one mixing device or by jet mixing. Preferably, a mixing device is an impeller. Preferably, liquid flow is upward through the stack and downward outside the stack (between the stack and the reactor walls). Preferably, impellers are on a shaft which passes through the center of the catalyst bed. In a preferred embodiment of the invention, the reactor is a CSTR and the base is added from the top of the reactor.

The OER typically produces MMA, along with methacrylic acid and unreacted methanol. Preferably, methanol and methacrolein are fed to the reactor containing the catalyst bed in a methanol:methacrolein molar ratio from 1:10 to 100:1, preferably from 1:2 to 20:1, preferably from 1:1 to 10:1. Preferably, the catalyst bed further comprises inert materials above and/or below the catalyst. Preferred inert materials include, e.g., alumina, clay, glass, silica carbide and quartz. Preferably, the inert material has an average diameter equal to or larger than that of the catalyst. Preferably, the reaction products are fed to a methanol recovery distillation column which provides an overhead stream rich in methanol and methacrolein; preferably this stream is recycled back to the OER. The bottoms stream from the methanol recovery distillation column comprises MMA, MDA, methacrylic acid, salts and water. In one embodiment of the invention, MDA is hydrolyzed in a medium comprising MMA, MDA, methacrylic acid, salts and water. MDA may be hydrolyzed in the bottoms stream from a methanol recovery distillation column; said stream comprising MMA, MDA, methacrylic acid, salts and water. In another embodiment, MDA is hydrolyzed in an organic phase separated from the methanol recovery bottoms stream. It may be necessary to add water to the organic phase to ensure that there is sufficient water for the MDA hydrolysis; these amounts may be determined easily from the composition of the organic phase. The product of the MDA hydrolysis reactor is phase separated and the organic phase passes through one or more distillation columns to produce MMA product and light and/or heavy byproducts. In another embodiment, hydrolysis could be conducted within the distillation column itself. Preferably, oxygen concentration at a reactor outlet is at least 1 volume %, preferably at least 2 volume %, preferably at least 3 volume %; preferably no more than 7 volume %, preferably no more than 6.5 volume %, preferably no more than 6 volume %. Preferably, the superficial velocity of liquid through the reactor is from 1 to 50 mm/s, preferably at least 2 mm/s, preferably at least 3 mm/s, preferably at least 4 mm/s, preferably at least 5 mm/s; preferably no more than 20 mm/s, preferably no more than 15 mm/s.

One preferred embodiment of the fixed bed reactor for oxidative esterification is a trickle bed reactor, which contains a fixed bed of catalyst and passes both the gas and liquid feeds through the reactor in the downward direction. In trickle flow, the gas phase is the continuous fluid phase. Thus, the zone at the top of the reactor, above the fixed bed, will be filled with a vapor phase mixture of nitrogen, oxygen, and the volatile liquid components at their respective vapor pressures. Under typical operating temperatures and pressures (50-90° C. and 60-300 psig), this vapor mixture is inside the flammable envelope if the gas feed is air. Thus, only an ignition source would be required to initiate a deflagration, which could lead to loss of primary containment and harm to the physical infrastructure and personnel in the vicinity. In order to address process safety considerations, a means to operate a trickle bed reactor while avoiding a flammable headspace atmosphere is operation with a gas feed containing a sufficiently low oxygen mole fraction to ensure the oxygen concentration in the vapor headspace is below the limiting oxygen concentration (LOC).

Knowledge of the LOC is required for the fuel mixture, temperature, and pressure of concern. Since the LOC decreases with increasing temperature and pressure, and given that methanol gives a lower LOC than the other two significant fuels (methacrolein and methyl methacrylate), a conservative design chooses a feed oxygen to nitrogen ratio that ensures a composition with less than the LOC at the highest expected operating temperature and pressure. For example, for a reactor operated at up to 100° C. and 275 psig (1990 kPa), the feed oxygen concentration in nitrogen should not exceed 7.4 mol %.

EXAMPLES

Example #1: Multi-Zone Tubular Reactor

A series of runs was conducted in which 20 wt % methacrolein, 200 ppm inhibitor, and a balance of methanol were fed to a catalytic zone consisting of ⅜" (9.6 mm) stainless steel tubular reactor containing a short front section of silica carbide and 10 g of catalyst followed by a mixing zone consisting of a 150 mL liquid volume stirred vessel with a pitch blade turbine, followed by a second catalytic zone consisting of ⅜" (9.6 mm) stainless steel tubular reactor containing a short front section of silica carbide and 10 g of catalyst. The catalyst consisted of 1.5 wt % Au on a Norpro 1mm diameter high surface area alumina spherical support. Air was fed to the first catalyst zone sufficient to have roughly 5 mol % oxygen in the outlet gas and a gas containing 8 mol % oxygen in nitrogen was feed to the second zone sufficient to have an outlet gas between 4 mol % and 5 mol % oxygen. The reactors were operated at 60° C. and 160 psig (1200 kPa). The pH at the exit of catalyst zone 1 was approximately 6.3. The product of the reactor was sent to a liquid-vapor separator and the vapor was sent to a condenser with liquid return. Results are described in the below table. A base consisting of sodium methoxide in methanol was added to the mixing zone in some cases. The mixing zone was stirred at 600 RPM in some cases and not stirred in other cases. Product MMA is the percent MMA among products originating as methacrolein reactant. Product Adducts is the percent Michael Adducts among products originating as methacrolein reactant. Space-time yield is in mol MMA per Kg catalyst hour.

| run | Base wt % NaOMe | Mix rate (rpm) | Feed (g/hr) | Base (g/hr) | Zone 2 Exit (pH) | Prod MMA (%) | Prod Adducts (%) | conv (%) | STY (m/Kghr) |
|---|---|---|---|---|---|---|---|---|---|
| 1 | na | 600 | 40 | 0 | 5.8 | 97.4 | 0.3 | 67 | 3.1 |
| 2 | 3 | 600 | 40 | 2 | 7 | 97.3 | 1.2 | 88 | 3.7 |
| 3 | 3 | 0 | 40 | 2 | 7.2 | 96.4 | 2.3 | 90 | 3.7 |

Example #2: Slurry Catalyst Continuous Stirred Tank Reactor

A series of runs was conducted in which 20 wt % methacrolein, 200ppm inhibitor, and a balance of methanol were fed to a continuous stirred tank reactor (CSTR) containing a slurry catalyst. The catalyst consisted of 5 wt % palladium, 2 wt % bismuth, and 1 wt % antimony on Puralox 5/90, an alumina support material. 20 g of catalyst was loaded in 150 mL of liquid in the stirred vessel. The stir rate of the reactor was altered and the production of Michael Adducts was measured. Air was fed to the reactor and oxygen in the vent was measured. Oxygen in the vent was approximately 1 mol % in all cases. The reactor was operated at 80° C. and 60 psig. The pH at the exit of the reactor was approximately 6.5, maintained by the addition of 1 wt % sodium methoxide in methanol. The off-gas of the reactor was sent to a condenser with liquid return to the reactor. Results are described in the below table. Product distribution for MMA is the percent MMA among products originating as methacrolein reactant. Product distribution for Michael Adducts is the percent adducts among products originating as methacrolein reactant. Space-time yield is in mol MMA per Kg catalyst hour. Characteristic mixing time is estimated to be well under one minute for runs 4 through 7.

| Run | RPM | STY (m/Kghr) | Prod Dist (Adducts %) | Prod Dist (MMA %) |
|---|---|---|---|---|
| 4 | 600 | 4.1 | 0.50 | 96 |
| 5 | 700 | 4.3 | 0.48 | 96 |
| 6 | 800 | 4.8 | 0.39 | 98 |
| 7 | 1200 | 4.5 | 0.31 | 97 |

Conclusions

Data obtained in the multi-zone reactor indicates that for base addition to the reactor, characteristic mixing time in the mixing zone(s) is an important parameter to decrease the formation of Michael Adducts and increase selectivity in general as measured here by product distribution to MMA. Michael Adduct formation roughly doubled when high characteristic mixing time in the mixing zone was utilized vs. more appropriate mixing at 600 RPM.

Data obtained in the stirred tank reactor indicates Michael Adduct formation can be reduced significantly by reduced characteristic mixing time.

The invention claimed is:

1. A method for preparing methyl methacrylate from methacrolein and methanol; said method comprising contacting in a reactor a mixture comprising methacrolein, methanol and oxygen with a catalyst bed of heterogeneous catalyst comprising a support and a noble metal, wherein base is added to the reactor while maintaining time to reach 95% homogeneity at no greater than 10 minutes.

2. The method of claim 1 in which the reactor is a continuous stirred tank reactor.

3. The method of claim 2 in which the reactor comprises at least one impeller having a tip speed from 0.1 to 10 m/s.

4. The method of claim 3 in which the catalyst bed is at a temperature from 40 to 120° C.

5. The method of claim 4 in which pH in the catalyst bed is from 4 to 8.

6. The method of claim 5 in which the catalyst has an average diameter from 200 microns to 10 mm.

7. The method of claim 6 in which the catalyst bed is surrounded by a solid baffle which allows liquid flow through the catalyst bed in one direction.

8. The method of claim 7 in which the height of the solid baffle is from 30 to 90% of height of the reactor.

9. The method of claim 8 in which time to reach 95% homogeneity is no greater than 4 minutes.

10. The method of claim 9 in which the noble metal is selected from the group consisting of gold and palladium.

* * * * *